United States Patent [19]

Clemens et al.

[11] Patent Number: 5,320,097
[45] Date of Patent: Jun. 14, 1994

[54] ENDOTRACHEAL TUBE HOLDING AND SECURING DEVICE

[75] Inventors: Paul J. Clemens, Decatur; Glenn A. Powell, Mattawan, both of Mich.

[73] Assignee: N.O.B. Inc., Decatur, Mich.

[21] Appl. No.: 980,995

[22] Filed: Nov. 24, 1992

[51] Int. Cl.$^5$ .................. A61M 16/00; A62B 9/06
[52] U.S. Cl. .................. 128/207.17; 128/DIG. 26; 128/912
[58] Field of Search .................. 128/200.26, 207.17, 128/911, 912, DIG. 26, DIG. 15; 604/177-179

[56] References Cited

U.S. PATENT DOCUMENTS

| | | | |
|---|---|---|---|
| 1,819,390 | 8/1931 | Seager. | |
| 2,908,269 | 10/1959 | Cheng | 128/207.17 |
| 3,302,968 | 2/1967 | Bleiman et al. | 294/87 |
| 3,760,811 | 9/1973 | Andrew | 128/DIG. 26 |
| 4,313,437 | 2/1982 | Martin | 128/207.17 |
| 4,331,144 | 5/1982 | Wapner | 128/DIG. 26 |
| 4,520,813 | 6/1985 | Young | 128/DIG. 26 |
| 4,774,944 | 10/1988 | Mischinski | 128/DIG. 26 |
| 5,026,352 | 6/1991 | Anderson | 128/DIG. 26 |

Primary Examiner—Edgar S. Burr
Assistant Examiner—Kimberly L. Asher
Attorney, Agent, or Firm—Woodard, Emhardt, Naughton, Moriarty & McNett

[57] ABSTRACT

An endotracheal tube holding and securing device is adjusted using a strap including mating hook and loop type fastener pads, such as sold under the TM VELCRO to hold an endotracheal tube in place after intubation has been performed. The endotracheal tube holder includes two identical hook-shaped members each having a hook portion. One hook-shaped member is inverted, superimposed and slidably connected to the second hook-shaped member. In this orientation, the curved faces of the hook-shaped members form a "C" shaped gripper used for holding the endotracheal tube. The hook and loop covered nylon strap is attached at the end of each hook-shaped member distant from the hook portion. The nylon strap is used both to secure the endotracheal tube holder to the patient's face and to apply a force at the end of each hook-shaped member that causes each member to slide in the direction of the applied force, causing the tube to be firmly gripped between the two curved faces of the two hook portions.

19 Claims, 3 Drawing Sheets

ENDOTRACHEAL TUBE HOLDING AND SECURING DEVICE

BACKGROUND OF THE INVENTION

This invention relates to an endotracheal tube holder and more particularly to a new and improved endotracheal tube holder suitable for use to assist the healthcare provider in holding and securing an endotracheal tube once intubation has been performed.

More particularly endotracheal tubes are commonly used by healthcare providers for providing an unobstructed passageway to facilitate breathing. The endotracheal tube is inserted into the patient's mouth and trachea in a process called intubation. It is very important that the endotrachial tube be securely maintained in this position during the entire period of use. Additionally, it may be necessary to insert endotracheal tubes under emergency conditions where time is of the essence.

Various devices exist which are designed to secure an endotracheal tube. U.S. Pat. No. 3,760,811 shows a disposable clamp for holding an endotracheal tube or the like that comprises a pair of superimposed wafer-like clamping members formed with complementary cut-away portions to define an aperture for receiving the tube. One problem with this device is that time is wasted assembling the interlocking clamp members around the tube. Additionally, once assembled, the clamping members can be separated only by breaking one of the clamping members.

U.S. Pat. No. 4,520,813 to Young shows an endotracheal tube holder comprising a pair of identical curved, plate-like hooking members and an interconnecting attachment band. Each of the hooking members has a dogleg opening for receiving and engaging the endotracheal tube when the hooking members are overlapped in position over the patient's mouth. Following intubation, the first hooking element is placed over the patient's mouth with its dogleg opening engaging the endotracheal tube. Then, the attachment band is pulled around the patient's face and neck and the second hooking element is placed over the patient's mouth with its dogleg opening engaging the endotracheal tube. Finally, a VELCRO patch is secured to a mating Velcro patch on the uppermost hooking element. A disadvantage to this method is that any four step process can become laborious and time consuming under emergency conditions.

U.S. Pat. No. 4,774,944 to Mischinski shows a holder for an endotracheal tube which is formed from a generally rigid flat bar having a lateral cut-out leaving a reduced flexible neck connecting the remaining bar portions together for relative swinging about an axis through the neck, the cut being configured to conformably receive and circumferentially clamp about a received tube. Additionally, one side edge of the bar being provided on respective bar portions with a releasably interengageable catch and a latch which automatically snap into interengagement upon relative swinging movement of the bar portions.

Additional references that may have some relevance are U.S. Pat. Nos. 1,819,390 to Seager, 2,908,269 to Cheng, 3,302,968 to Bleiman et al., 4,313,437 to Martin, 4,331,144 to Wapner and 5,026,352 to Anderson.

It is therefore desirable to have an endotracheal tube holder that is generally uncomplicated to use and can be applied quickly and easily in emergency situations.

SUMMARY OF THE INVENTION

One embodiment of the endotracheal tube holding and securing device might involve a flexible body formed from two identical hook-shaped members engaged so that the faces of the hook portions of each hook-shaped member face each other. The two opposing hook faces are designed to abut an endotracheal tube and to grip the tube therebetween. Pins maintain the hook-shaped members in close contact while additionally allowing the hook-shaped members to slide back and forth relative to one another. The device is secured to the patient's head by a securement strap. Additionally, the securement strap provides a force on each hook-shaped member, resulting in the hook faces gripping the endotracheal tube.

Another aspect of the present invention is a method of making an endotracheal tube holding and securing device wherein two identical hook-shaped members having hook faces designed to abut a tube are engaged such that their hook faces face one another. The hook-shaped members are fastened together in slidable contact. A securement strap is provided to enable the endotracheal tube holding and securing device to be secured around the head of a patient and to apply a force on each hook-shaped member in a direction away from the endotracheal tube. The applied force causes each hook-shaped member to slide resulting in the hook faces of the hook-shaped members gripping the endotracheal tube.

An object of the present invention is to provide an improved endotracheal tube holder.

A further object of the present invention is to provide an endotracheal tube holder that may be used to maintain an endotracheal tube after intubation by tightening a securement strap attached to the endotracheal tube holder.

Further objects and advantages of the present invention will be evident from the following written description and accompanying figures.

DESCRIPTION OF THE PREFERRED EMBODIMENT

Figure 1:
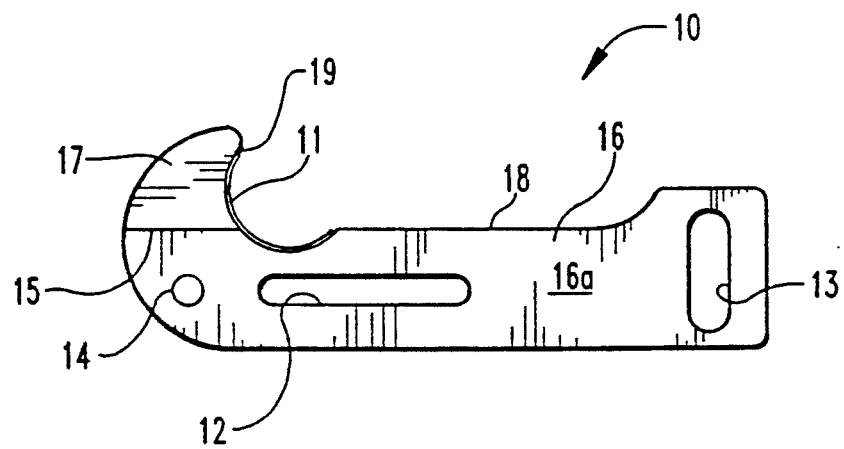
FIG. 1 is a front elevational view of a hook-shaped member forming a part of an endotracheal tube holding and securing device in accordance with one embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 4:
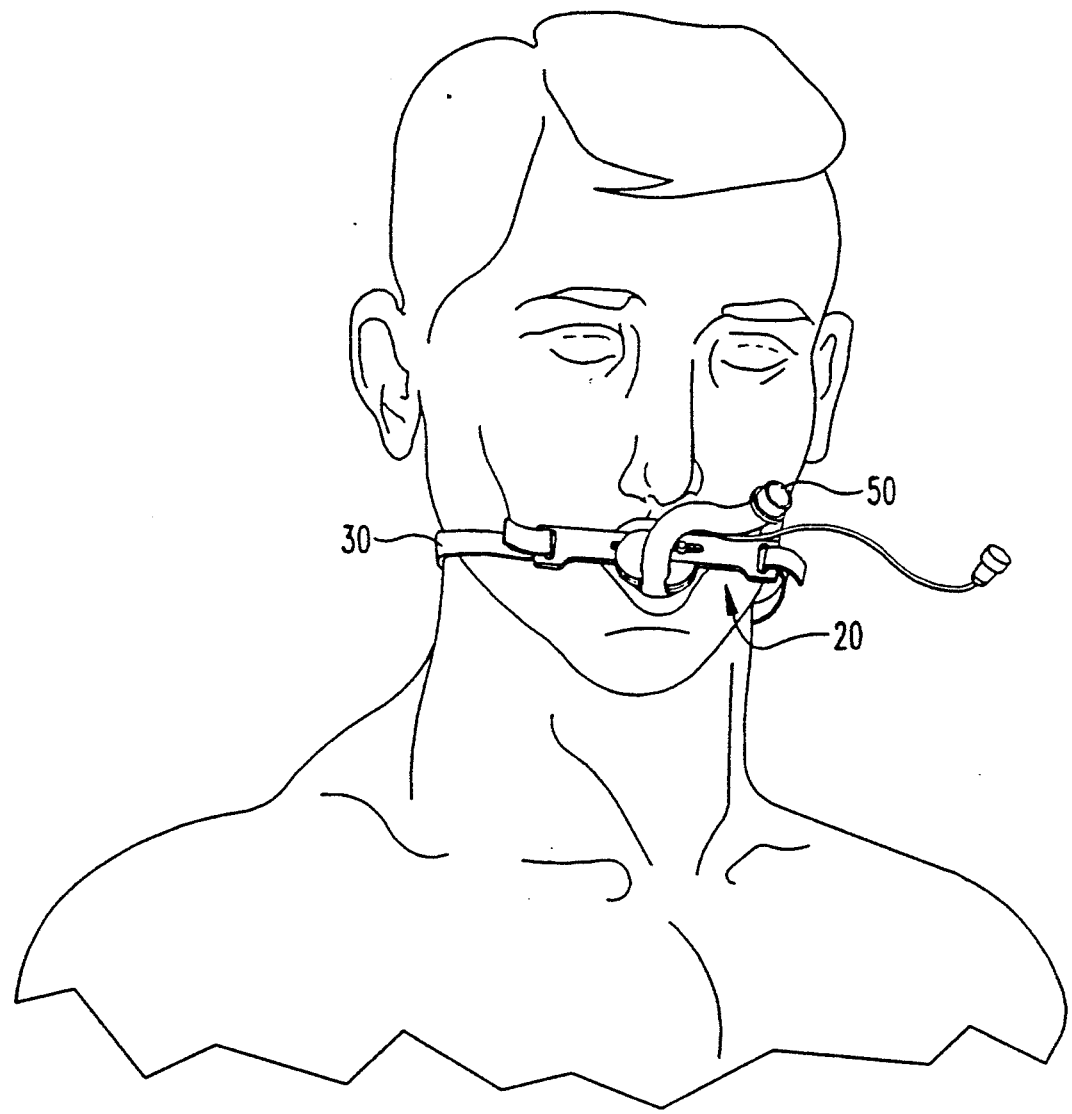
FIG. 4 is a perspective view of the endotracheal tube holding and securing device secured around the head of a patient and holding an endotracheal tube after intubation.

In one embodiment of the present invention, an endotracheal tube holder 20 is provided to assist a healthcare provider in holding and securing an endotracheal tube once intubation has been performed (FIG. 4). The device 20 consists of two superimposed hook-shaped members, 10 and 110, that are secured to each other in a manner that allows each piece to slide freely relative to the other when a force is applied and to create an opening and closing motion for gripping a tube.

Figure 2:
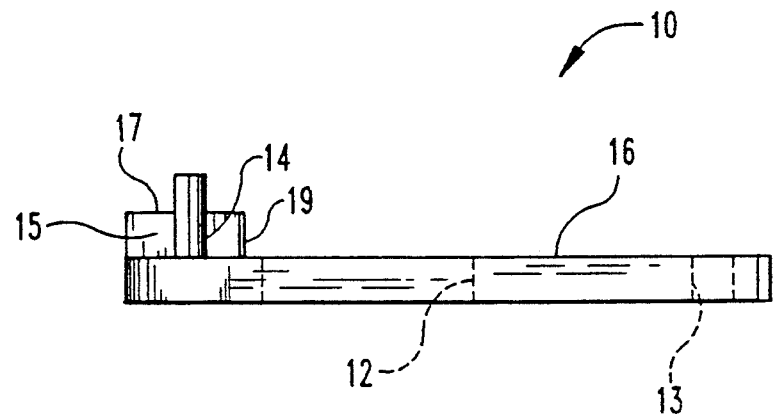
FIG. 2 is a side elevational view of the hook-shaped member of FIG. 1.

Referring now to FIGS. 1 and 2, there is shown an integrally molded or formed hook-shaped member 10 having a body portion 16 and a hook portion 17. In the preferred embodiment of the present invention, body portion 16 includes an outer surface 16a and an edge 18. Additionally, body portion 16 has therethrough a slide slot 12, and a securement or strap slot 13. Pin 14 is fixedly mounted in an appropriate bore in the body 16 and extends from the body at the end closest to hook portion 17. Slide slot 12 is aligned with pin 14 and is additionally located along the length of body 16. Securement slot or strap slot 13 passes through body 16 at the end of the hook-shaped member 10 most distant from hook portion 17. Additionally, strap slot 13 is arranged in perpendicular relation to slide slot 12.

Hook portion 17 of hook-shaped member 10 initially extends perpendicular from body portion 16 and curves towards body portion 16 forming a curved face 19 which is designed to abut a tube. A portion of edge 18 may be curved so as to continue the curvature of curved face 19. Hook portion 17 has a thickness greater than the thickness of the body portion 16 forming a face 15 as part of hook portion 17 which face extends away from and is perpendicular to the outer surface 16a of body portion 16. The inside area of curved face 19 may be coated with a rubber material 11 to prevent the endotracheal tube from slipping.

Figure 3:
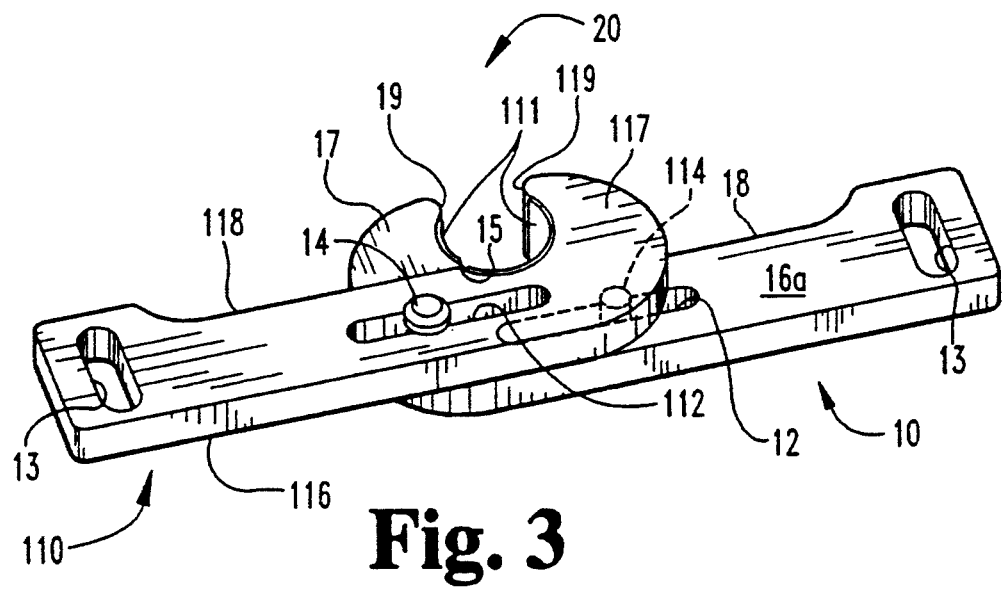
FIG. 3 is a perspective view of an endotracheal tube holder in accordance with the present invention but showing it without a strap forming a part thereof.

Referring now to FIG. 3 the endotracheal tube holder 20 is shown as consisting of two identical hook-shaped members, 10 and 110, of the form shown in FIGS. 1 and 2. A first hook-shaped member 110 is inverted with relation to the orientation displayed in FIG. 1 and engaged with a second hook-shaped member 10 such that outer surface 116a of hook-shaped member 110 contacts outer surface 16a of hook-shaped member 10. Additionally, this orientation enables the face 15 of hook-shaped member 10 to engage edge 118 of hook-shaped member 110. Likewise, the face (not shown) of hook-shaped member 110 which corresponds to face 15, engages edge 18 of hook-shaped member 10. Pin 14 extends through slot 112 of hook-shaped member 110 and is stamped (so as to make an enlarged head) to fasten member 110 to member 10. Similarly, pin 114 extends through slot 12 of hook-shaped member 10 and is stamped to fasten member 10 to member 110. Pins 14 and 114 are of sufficient length to maintain hook-shaped member 110 in close contact with hook-shaped member 10, while still allowing hook-shaped member 110 to slide over hook-shaped member 10. As a result of securing the hook-shaped members together in the interlocking fashion described above, curved faces 19 and 119 face each other in an opposing fashion and, together with the curvature present at edges 18 and 118, form a "C" shaped gripper 111 designed to grip the endotracheal tube.

Figure 5:
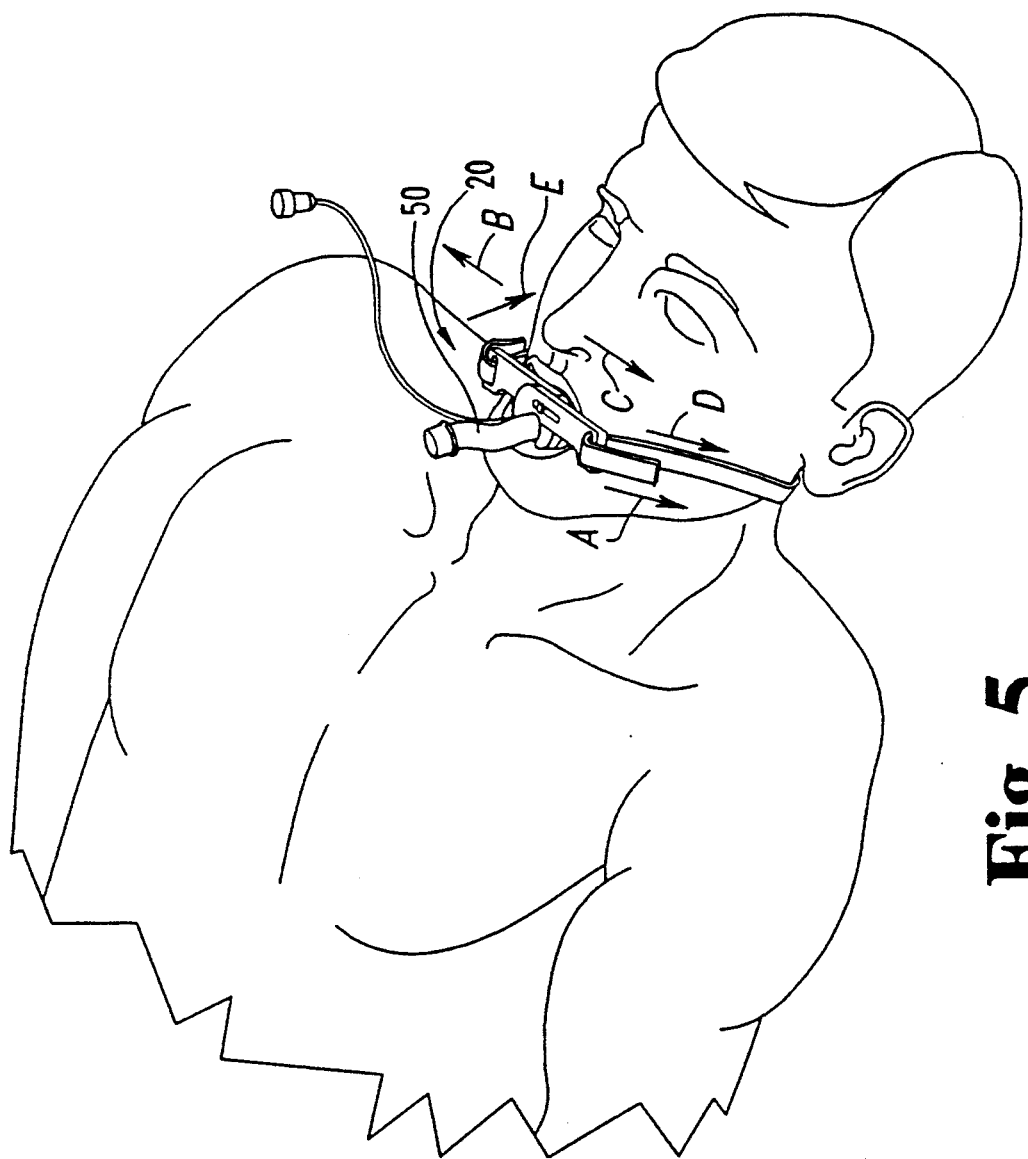
FIG. 5 is a further perspective view of the endotracheal tube holding and securing device showing it on a patient and from a different angle than FIG. 4.

As shown in FIGS. 4 and 5, a nylon strap 30 is placed through strap slots 13 located at the end of each hook-shaped member opposite the end having the hook portion. Hook and loop type fastener pads, such as are sold under the tradename VELCRO, are attached along nylon strap 30 in a mating configuration so as to permit the attachment of strap 30 to endotracheal tube holder 20. One end of the nylon strap 30 is passed through each strap slot 13. The hook and loop type fastener pads are then mated to secure the strap 30 to the endotracheal tube holder 20. The strap can be adjusted in a known fashion to allow the strap to be shortened or lengthened, according to the size of the patient's head and the amount of force needed to cause the gripper 111 to securely grip the tube 50. FIG. 5 shows the manner and direction (according to direction arrow A) in which the strap 30 is tightened.

In operation, after intubation has been performed, the nylon strap 30 is placed around the patient's head with the endotracheal tube holder 20 placed over the patient's mouth cavity. The "C" shaped gripper 111, initially loosely extended, is placed adjacent to the tube 50. The strap 30 is tightened causing forces B and C to be applied at the strap-bearing ends of each hook-shaped member 10 and 110 in the direction of the strap 30. As such, the force created on the first hook-shaped member is opposite the force created on the second hook-shaped member. These opposing forces cause each hook-shaped member 10 and 110 to slide with respect to each other and in the direction of the applied forces. This results in the "C" shaped gripper 111 firmly gripping the tube 50. Strap 30 can be loosened or tightened to provide the amount of force desired for causing the "C" shaped gripper 111 to tighten around the endotracheal tube 50.

Additionally, the forces D and E created by the strap 30 causes the endotracheal tube holder 20 to rest between the lips and teeth and slightly into the mouth of the patient, stretching from one corner of the mouth to the other (FIG. 4). As this is desired, the tube holder 20 is designed to be of a sufficiently small size so as to be able rest slightly within the mouth of the patient while leaving the mouth cavity accessible in the event that a suctioning catheter should need to be used in the patient's mouth.

While the invention has been illustrated and described in detail in the drawings and foregoing description, the same is to be considered as illustrative and not restrictive in character, for example, although two pins are used in the preferred embodiment, it is understood that the invention would work with only one pin. Similarly, it is understood that the invention would work without the curvature in body portion 16 along edge 18. It is therefore understood that only the preferred embodiment has been shown and described and that all changes and modifications that come within the spirit of the invention are desired to be protected.

What is claimed is:

1. An endotracheal tube holder comprising:
    a first hook-shaped member located along an axis defined through the length of said first hook-shaped member, said first hook-shaped member including a first hook portion and a first body portion, said first hook portion initially extending perpendicularly from said first body portion and curving towards said first body portion to form a curved face for abutting a tube;

a second hook-shaped member located along said axis, wherein said axis additionally runs through the length of said second-hook shaped member, said second hook shaped member being identical to said first hook-shaped member and including a second hook-shaped portion having a second curved face and a second body portion;

said first and said second hook-shaped members each having a slide slot therethrough; and, connector means connected between said first hook-shaped member and said second hook-shaped member and extending through each said slide slot and located perpendicular to said axis, said connector means connecting said first hook-shaped member to said second hook-shaped member when said first hook-shaped member is in an inverted superimposed position relative to said second hook-shaped member, said first hook-shaped member sliding in a first direction along said axis and said second hook-shaped member sliding in an opposite direction along said axis, wherein said curved face of said first hook-shaped member and said curved face of said second hook-shaped member slide towards each other along said axis and form a "C" shaped configuration for gripping said tube said first and said second hook-shaped members sliding along said axis by means of said perpendicular connector means and said slide slots.

2. An endotracheal tube holder comprising:

a first hook-shaped member including a first hook portion and a first body portion, said first hook portion initially extending perpendicularly from said first body portion and curving towards said first body portion to form a curved face for abutting a tube, said first body portion including a slide slot therethrough;

a second hook-shaped member identical to said first hook-shaped member having a second hook-shaped portion having a second curved face and a second body portion, said second body portion having a slide slot therethrough; and, connector means for connecting said first hook-shaped member to said second hook-shaped member when said first hook-shaped member is in an inverted superimposed position relative to said second hook-shaped member, and wherein said curved face of said first hook-shaped member and said curved face of said second hook-shaped member form a "C" shaped configuration for gripping said tube, said connector means includes a pin extending from said first body portion of said first hook-shaped member and through said slide slot of said second hook-shaped member for maintaining said first body in slidable contact with said second body.

3. The endotracheal tube holder according to claim 2 wherein said connector means additionally comprises a second pin extending from said second body portion of said second hook-shaped member and through said slide slot of said first hook-shaped member for maintaining said first body in slidable contact with said second body.

4. The endotracheal tube holder according to claim 2, further comprising a securement strap, wherein said first body portion additionally includes a first attachment means, and wherein said second body portion additionally includes a second attachment means, said first and second attachment means attaching said securement strap between said first hook-shaped member and said second hook-shaped member of said endotracheal tube holder.

5. The endotracheal tube holder according to claim 4 wherein said first attachment means includes a first securement slot therethrough and said second attachment means includes a second securement slot therethrough.

6. The endotracheal tube holder according to claim 5 wherein said securement strap comprises a strap portion having a first strap end including a hook type fastener and a corresponding loop type fastener, said strap portion additionally having a second strap end including a hook type fastener and a corresponding loop type fastener, wherein said first strap end is placed through said first securement slot and said second strap end is placed through said second securement slot and said hook and loop type fasteners are mated to attach said strap portion to said first and second body portions.

7. The endotracheal tube holder according to claim 6 wherein said first hook portion additionally comprises a first face perpendicular to said first body portion and said second hook portion additionally comprises a second face perpendicular to said second body portion, wherein said body portion of said second hook-shaped member engages said first face and wherein said body portion of said first hook-shaped member engages said second face.

8. The endotracheal tube holder according to claim 6 wherein a portion of the body of said endotracheal tube holder fits into the mouth of a patient.

9. The endotracheal tube holder according to claim 6 wherein each of said first curved face and said second curved face includes a rubber coating to prevent slipping of said tube.

10. A method for constructing an endotracheal tube holder comprising the steps of:

providing a first hook-shaped member comprising a body portion and a hook portion, said body portion including a slide slot and a securement slot therethrough, said hook portion including a first curved face for abutting a tube;

providing a second hook-shaped member identical to said first hook-shaped member comprising a second body portion and a second hook portion, said second body portion including a slide slot and a securement slot therethrough, said second hook portion comprising a second curved face for abutting a tube;

inverting said first hook-shaped member with respect to said second hook-shaped member and laying said first hook-shaped member over said second hook-shaped member, said body portions of said first hook-shaped member and said second hook-shaped member extending along the same axis, said first curved face opening in a direction opposing the opening of said second curved face, and additionally, said first and said second curved faces together forming a single "C" shaped gripper for grasping an endotracheal tube;

providing a connector means located perpendicular to said axis; and, fastening said first hook-shaped member to said second hook-shaped member with said connector means extending through said slide slots, said connector means and said slide slots maintaining said first hook-shaped member in sliding contact with said second hook-shaped member, said first hook-shaped member sliding in a first direction along said axis and said second hook-shaped member sliding in a second direction along said axis, said second direction being opposite to said first direction.

11. The method of claim 10 additionally comprising the step of attaching a securement means through said securement slot of said first body and through said securement slot of said second body for securing said device around the head of a patient.

12. An endotracheal tube holder comprising:
   a first hook-shaped member comprising:
   a first body portion including a slide slot and a securement slot;
   a first hook portion initially extending from said first body portion and curving towards said body portion to form a first curved face for abutting a tube, and additionally including a first face for engaging a second body of a second hook-shaped member;
   a second hook-shaped member comprising:
   a second body portion having a slide slot and a securement slot; and,
   a second hook portion initially extending from said second body portion and curving towards said second body portion to form a second curved face for abutting a tube, and additionally including a second face for engaging said first body of said first hook-shaped member;
   wherein said second curved face is disposed opposite said first curved face and wherein said first curved face and said second curved face together form a "C" shaped configuration for gripping said tube; and,
   a first pin extending from the body portion of said first hook-shaped member and through said slide slot of said second body portion of said second hook-shaped member for maintaining slidable contact between said first and said second bodies.

13. The endotracheal tube holder according to claim 12 wherein said first face for engaging is perpendicular to said first body portion, and wherein said second face for engaging is perpendicular to said second body portion, and wherein said second body portion engages said second face for engaging and wherein said first body engages said second face for engaging.

14. The endotracheal tube holder according to claim 12 additionally comprising a second pin extending from the body portion of said second hook-shaped member and through said slide slot of said first body portion of said first hook-shaped member for maintaining slidable contact between said first and said second body portions of said first and second hook-shaped members.

15. The endotracheal tube holder according to claim 14 wherein said first and said second hook-shaped members are identical.

16. The endotracheal tube holder according to claim 15 wherein said device additionally comprises a securement band attached to said first and second body portions through said first and second securement slots.

17. The endotracheal tube holder according to claim 16 wherein said securement band comprises an elastic band having corresponding compatible hook and loop type fasteners.

18. The endotracheal tube holder according to claim 17 wherein a portion of the body of said endotracheal tube holder fits into the mouth of a patient.

19. The endotracheal tube holder according to claim 18 wherein said first and said second curved faces include a non-slip coating.

* * * * *